(12) United States Patent
Howard et al.

(10) Patent No.: US 7,389,672 B2
(45) Date of Patent: Jun. 24, 2008

(54) METHOD AND APPARATUS FOR THERMAL ISOLATION OF A GAS SENSOR

(75) Inventors: Timothy Howard, Canyon Country, CA (US); Robert Pendergrass, Saugus, CA (US); Carlton Salter, Stevenson Ranch, CA (US)

(73) Assignee: H2scan Corporation, Valencia, CA (US)

( * ) Notice: Subject to any disclaimer, the term of this patent is extended or adjusted under 35 U.S.C. 154(b) by 127 days.

(21) Appl. No.: 11/046,371

(22) Filed: Jan. 27, 2005

(65) Prior Publication Data

US 2005/0210656 A1    Sep. 29, 2005

Related U.S. Application Data

(60) Provisional application No. 60/540,019, filed on Jan. 27, 2004.

(51) Int. Cl.
*G01N 7/00* (2006.01)
(52) U.S. Cl. .................................... 73/23.21
(58) Field of Classification Search .............. None
See application file for complete search history.

(56) References Cited

U.S. PATENT DOCUMENTS

| | | | |
|---|---|---|---|
| 4,596,975 A | | 6/1986 | Reddy et al. |
| 4,776,214 A | * | 10/1988 | Moran et al. ............. 73/204.11 |
| 5,279,795 A | | 1/1994 | Hughes et al. |
| 5,659,127 A | | 8/1997 | Shie et al. |
| 5,837,886 A | * | 11/1998 | Nakahara et al. ........... 73/31.06 |
| 6,067,843 A | * | 5/2000 | Hafele et al. ............... 73/31.05 |
| 6,202,467 B1 | | 3/2001 | Iovdalsky et al. |
| 2005/0109081 A1 | * | 5/2005 | Zribi et al. ................ 73/31.05 |

FOREIGN PATENT DOCUMENTS

| | | |
|---|---|---|
| DE | 10122487 A1 | 11/2002 |
| WO | WO-01/02895 A | 4/2001 |

OTHER PUBLICATIONS

Hughes, Robert C. et al., "Sensors for Detecting Molecular Hydrogen Based on Pd Metal Alloys", Sandia National Laboratories, Microsensor Research and Development Department, Albuquerque, NM, 1997.
W L Gore & Associates, "GORE™ Membrane Vents, Series HPM: High Protection Against Metal Impact" Product Data Sheet, 2002.

* cited by examiner

*Primary Examiner*—Robert R Raevis
(74) *Attorney, Agent, or Firm*—McAndrews, Held & Malloy, Ltd.

(57) ABSTRACT

A gas sensor assembly detects the presence of a constituent in a first gas stream. The assembly comprises: (a) a flexible circuit having a pair of oppositely-facing surfaces, (b) a sensor mounted on one surface of the flex circuit, the sensor electrically connected to conductors in the flex circuit, and (c) a channel for directing a second gas stream across the flex circuit surface facing away from the sensor, the channel formed at least in part by the flex circuit surface facing away from the sensor. The first and second gas streams can be derived from a common gas stream. In operation, thermal conductivity between the sensor and neighboring heat-conducting structures components is reduced, thereby reducing sensor electric power consumption.

18 Claims, 1 Drawing Sheet

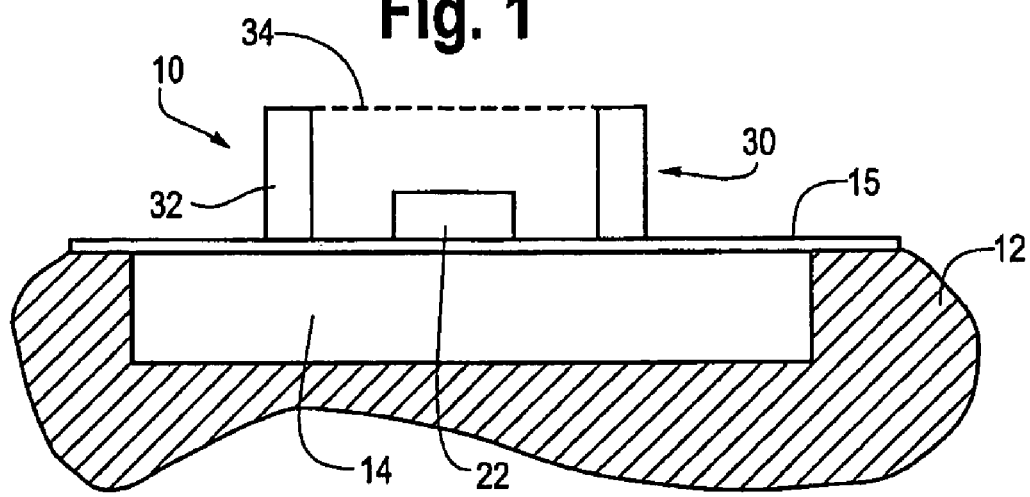
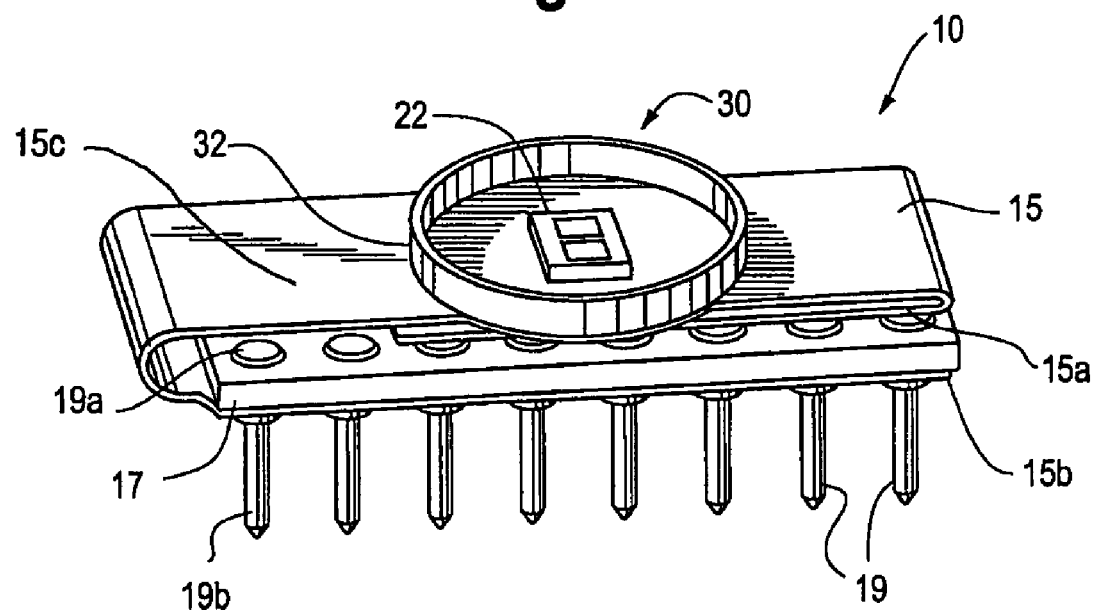

METHOD AND APPARATUS FOR THERMAL ISOLATION OF A GAS SENSOR

CROSS-REFERENCE TO RELATED APPLICATION(S)

This application is related to and claims priority benefits from U.S. Provisional Patent Application Ser. No. 60/540,019, filed on Jan. 27, 2004. The '019 provisional application is hereby incorporated by reference herein in its entirety.

FIELD OF THE INVENTION

The present invention relates to sensors for detecting the presence of a constituent in a gaseous stream. More particularly, the present invention relates to a thermally-isolated gas sensor configuration in which the sensor is mounted on a flexible circuit having a gas-filled gap formed beneath the surface of the flex circuit that faces away from the sensor.

BACKGROUND OF THE INVENTION

In certain gas sensor applications, it is desirable to keep the sensor isolated from the external environment without impeding its functionality. Such isolation can be for the purpose of reducing or minimizing heat loss, reducing or minimizing the amount of light reaching the sensor, and/or reducing or minimizing the consequences of mechanical intrusion. Often, a sensor is operated at a given temperature, typically greater than that of the surrounding gas stream it is sensing. This is sometimes accomplished by the use of heat-producing devices disposed on the same substrate as the sensor. When this is the case, there is a finite amount of heat lost to the gas stream surrounding the sensor, as well as to the components and structures in thermal (and electrical) contact with the sensor. This heat loss is proportional to magnitude of power loss from the entire system in which the sensor has been incorporated. It is therefore desirable to reduce or minimize such heat loss from the sensor.

Conventional, prior art thermal isolation techniques include fabricating the sensor itself in such a way as to create structures to provide thermal isolation (see, for example, U.S. Pat. Nos. 5,211,053, 5,464,966, 5,659,127, 5,883,009 and 6,202,467). Such exemplary thermal isolation techniques were designed specifically for the type of construction of the sensor involved and did not overcome the problems associated with heat loss at an assembly level, that is, where the sensor is configured as part of a greater assembly. Prior implementations of such gas-sensing devices, such as catalytically-based gas sensors, have employed different techniques to thermally isolate the device, such as suspending the device, within the gas stream being sensed, using individual wires that electrically connect the sensing device to its downstream processing and control circuitry (see, for example, U.S. Pat. No. 5,902,556), but these methods are not preferred for a sensor with multiple connections.

Suspending a sensor by, for example, three to six individual wires to thermally isolate the sensor is problematic in configurations involving multiple sensor elements. In particular, multi-element sensor configurations have a large number of leads associated with the sensor, making it difficult to achieve an adequate degree of thermal isolation, in the volume provided, because the greater number of leads tends to conduct significant amounts of heat away from the sensor. Fabricating such a suspended assembly is prohibitively costly and overly complex.

Prior art gas sensor configurations with multi-element sensors mounted on a ceramic base or suspended by leads have been unable to achieve an adequate degree of thermal isolation such that the power requirements of the gas sensor configuration can be significantly reduced. Such prior art configurations typically involved bonding the sensor to a ceramic element, sometimes referred to "dual in-line package" in which two rows of pin connectors extend from a ceramic substrate. The pin connectors of the dual in-line package align with and are insertable into mounting holes in standard circuit boards. Prior art gas sensor configurations therefore exhibit undesirably high thermal losses and require greater amounts of power to compensate for such thermal losses.

SUMMARY OF THE INVENTION

The present gas sensor assembly has a configuration in which the sensor is thermally isolated, and overcomes one or more of the foregoing shortcomings of prior art gas sensors. In particular, the present thermally isolated gas sensor assembly reduces power consumption by employing a configuration in which the sensor is mounted on a flex circuit having conductors (copper traces) incorporated therein for electrically connecting the sensor to downstream processing and control circuitry. The present assembly has a gas-filled gap formed beneath the flex circuit surface facing away from the sensor. The sensor is mounted on the flex circuit and is electrically connected to the flex circuit by wire bonding. The present configuration thus provides thermal isolation of the sensor from its neighboring components and structures.

In one embodiment, a gas sensor assembly for detecting the presence of a constituent in a first gas stream comprises:
(a) a flexible circuit having a pair of oppositely-facing surfaces;
(b) a sensor mounted on one surface of the flex circuit, the sensor electrically connected to conductors in the flex circuit;
(c) a channel for directing a second gas stream across the flex circuit surface facing away from the sensor, the channel formed at least in part by the flex circuit surface facing away from the sensor.

In operation, thermal conductivity between the sensor and neighboring heat-conducting structures components is reduced, thereby reducing sensor electric power consumption.

In a preferred embodiment of the present gas sensor assembly, the first and second gas streams are derived from a common gas stream.

In another preferred embodiment of the present gas sensor assembly, the oppositely-facing surfaces of the flex circuit are planar.

A method for thermally isolating a gas sensor for detecting the presence of a constituent in a first gas stream comprises:
(a) mounting a sensor on a surface of a flexible circuit having a pair of oppositely-facing surfaces;
(b) directing within a channel a second gas stream across the flexible circuit surface facing away from the sensor, the channel formed at least in part by the flexible circuit surface facing away from the sensor.

In a preferred embodiment of the present method, the first and second gas streams are derived from a common gas stream.

BRIEF DESCRIPTION OF THE DRAWING(S)

FIG. 1 is a schematic diagram showing a cross-sectional view of a first basic configuration of the present thermally isolated gas sensor.

FIG. 2 is a perspective view of one embodiment of a gas sensor assembly that implements the configuration illustrated schematically in FIG. 1.

DETAILED DESCRIPTION OF PREFERRED EMBODIMENT(S)

Gas sensors of the type involved here generally exhibit three heat loss mechanisms: (a) convection from the top, (b) conduction through the bond wires to the copper traces in the flexible circuit, and (c) conduction through the connection of the sensor to the flexible circuit. The flex circuit can, in turn, dissipate heat by conduction to the edges of the flex circuit that connect the flex circuit to the circuit board or mounting hardware, by conduction through the copper traces to the same circuit board or hardware, and by convection from the surfaces of the flex circuit. The flex circuit provides a flexible means of controlling these losses to the required degree. The long copper traces and high thermal resistance of the flex circuit provide a significantly greater degree of thermal resistance compared to normal mounting of sensor to a semiconductor package. In addition, conduction through the flex circuit and traces can be reduced by making the traces longer and smaller in area. Convection to the surrounding air can be reduced by minimizing the area of the flex circuit and by providing a still air environment around the flex circuit to minimize the heat transfer.

Turning to FIG. 1, a gas assembly 10 has a gas-filled gap defined by the geometric configuration of the components to reduce or minimize heat loss. Specifically, a gas sensor 22 is mechanically and electrically attached to a flex circuit 15 that is suspended over a volume or gap 14 through which a gaseous stream can be directed. The gas stream can be either or both of the atmosphere being sensed and/or some other gas stream. The presence of gap 14 reduces or minimizes direct heat conduction between sensor 22 and its neighboring circuit components (designated generally in FIG. 1 by the numeral 12). Gas-filled gap 14 thermally isolates sensor 22 because gases are generally on the order of 10 to 100 times less heat-conductive than solids. The use of a flex circuit permits the use of various configurations to form the gas-filled gap.

As depicted in FIG. 1, gas sensor assembly 10 includes a sensor 22 that is mounted on a surface of flex circuit 15 and that is suspended over gas-filled gap 14 having a fixed volume. FIG. 1 also shows gas sensor assembly as having an enclosing structure 30 mounted on the surface of flex circuit 15 and that circumscribes sensor 22. Enclosing structure 30 includes a walled component 32, and a gas-permeable membrane 34, as depicted. An interior volume is formed within enclosing structure 30, bounded on the bottom by flex circuit 15 and sensor 22, bounded on the side by the walls of component 32, and bounded on the top by membrane 34.

FIG. 2 is a perspective view of one embodiment of a gas sensor assembly that implements the configuration illustrated schematically in FIG. 1. As shown in FIG. 2, sensor 22 is mounted at a central portion of the longitudinal extent of flex circuit 15. End portion 15a of flex circuit 15 is folded under the central portion containing sensor 22 to create a structure in which folded-under end portion 15a supports central portion 15c and prevents central portion 15c from contacting the underlying components of assembly 10. The support afforded by folded-under end portion 15a also enables a gas-filled gap or volume to be maintained under the central portion of flex circuit 15 with sensor 22 mounted thereon, thus thermal isolating sensor 22 from the underlying components of assembly 10.

As further shown in FIG. 2, flex circuit 15 terminates in an end portion 15b, in which the copper traces (not shown) that extend from sensor 22 are electrically connected to pin connectors 19. Each pin connector has a head portion 19a and a spiked portion 19b. In the illustrated embodiment, a copper trace extending from gas sensor 22 is electrically connected to pin connector head 19a. The spiked portions of pin connectors 19 are inserted through holes in end portion 15b of flex circuit 15, then through aligned holes in an electrically insulative support layer 17. The spiked portions of pin connectors 19 are insertable into aligned mounting holes in a circuit board (not shown), which contains the downstream processing and control circuitry to which the signals from sensor 22 are directed.

Persons skilled in the technology involved here will recognize that many other configurations of the flex circuit can provide the gas-filled gap for thermally isolating the sensor mounted thereon.

The present thermally isolated gas sensor assembly, in which one or more surfaces of a flex circuit on which the sensor is mounted define an gas-filled gap, is distinguished from prior art designs in which the sensor is suspended away from the neighboring circuit components by individual wires.

In the case of a sensor mounted to a standard semiconductor package, the thermal resistance of the flex circuit configuration offers considerably increased thermal isolation. Generally, the standard packaging is designed to pull heat out of the sensor, not to facilitate the retention of heat. In the case of sensors suspended by wires, the flex circuit offers considerable advantage for sensors that have multiple wires. Typically, wire suspended sensors have only four wires. The flex circuit approach allows for many wires. The increase in wires facilitates multiple sensors on one gas sensor assembly, with each sensor employing four-wire sensing, and in which the sensor wires are independent of the power supply wires. This approach provides enhanced accuracy and stability.

Although the present device has been implemented in its preferred embodiment to sense hydrogen, persons skilled in the technology involved here will recognize that one or more aspects of the present device could be implemented or readily modified to sense and/or detect the presence and/or amount of constituents in fluid streams generally, including gas streams containing hydrogen and/or other than hydrogen, liquid streams, liquid streams containing entrained gas(es) and/or solid(s), gas streams containing entrained liquid(s) and/or solid(s). Moreover, aspects of the present device could be implemented or readily modified to sense and/or detect the presence and/or amount of fluid constituents residing in the pores and/or lattice structure of solids.

While particular steps, elements, embodiments and applications of the present invention have been shown and described, it will be understood, of course, that the invention is not limited thereto since modifications can be made by those skilled in the art, particularly in light of the foregoing teachings.

What is claimed is:

1. A gas sensor assembly for detecting the presence of a constituent in a gas stream, the assembly comprising:
   (a) a flexible circuit having a pair of oppositely-facing surfaces;
   (b) a sensor having a top and a bottom surface, said sensor bottom surface mounted on said flexible circuit such that said flexible circuit underlies said sensor bottom surface in its entirety, and wherein said sensor is electrically connected to conductors in said flexible circuit; and
   (c) a gas-filled gap bordered on a top side at least in part by said flexible circuit surface opposite said sensor and bordered on a bottom side at least in part by other electrical components with which the sensor cooperates;
   whereby thermal conductivity between said sensor and said other electrical components is reduced, thereby reducing sensor electric power consumption.

2. The gas sensor assembly of claim 1 wherein said gas stream and gas in said gas-filled gap are derived from a common gas stream.

3. The gas sensor assembly of claim 1 wherein said oppositely-facing surfaces are planar.

4. The gas sensor assembly of claim 1 further comprising an enclosing structure mounted on said flexible circuit surface wherein said enclosing structure circumscribes said sensor.

5. The gas sensor assembly of claim 4 wherein said enclosing structure comprises a walled component and a gas-permeable membrane.

6. The gas sensor assembly of claim 1 wherein said constituent detected by said sensor is hydrogen.

7. The gas sensor assembly of claim 1 wherein said sensor is mounted at a central portion of said flexible circuit.

8. The gas sensor assembly of claim 7 wherein a portion of said flexible circuit is folded under said flexible circuit portion opposite the sensor bottom surface.

9. The gas sensor assembly of claim 1 wherein said flexible circuit contains copper traces.

10. The gas sensor assembly of claim 9 wherein said other electrical components include pin connectors electrically connected to said copper traces.

11. The gas sensor assembly of claim 10 wherein each of said pin connectors has a head portion and a spiked portion.

12. The gas sensor assembly of claim 11 wherein said copper traces are electrically connected to said pin connector head portions.

13. The gas sensor assembly of claim 11 wherein said pin connector spiked portions are inserted through holes in an end portion of said flexible circuit.

14. The gas sensor assembly of claim 1 where thermal conductivity between said sensor and said other electrical components is reduced in a vertical direction.

15. A method for thermally isolating a gas sensor for detecting the presence of a constituent in a gas stream, the method comprising:
 (a) mounting a sensor on a surface of a flexible circuit having a pair of oppositely-facing surfaces, said sensor having a top portion and a bottom portion such that said flexible circuit underlies said sensor bottom surface in its entirety;
 (b) creating a gas-filled gap bordered on a top side at least in part said flexible circuit surface opposite said sensor and bordered on a bottom side at least in part by other electrical components with which said sensor cooperates;
 wherein thermal isolation occurs between said other electrical components and said sensor.

16. The method of claim 15 wherein said gas stream and gas in said gas-filled gap are derived from a common gas stream.

17. The method of claim 15 wherein thermal isolation occurs between said other electrical components and said sensor in a vertical direction.

18. The method of claim 15 wherein said constituent detected by said sensor is hydrogen.

\* \* \* \* \*